(12) United States Patent
Fournier et al.

(10) Patent No.: US 9,880,117 B2
(45) Date of Patent: Jan. 30, 2018

(54) MEASURING INSTRUMENT FOR DETECTION OF ELECTRICAL PROPERTIES IN A LIQUID

(71) Applicant: 2351161 ONTARIO LIMITED, Scarborough (CA)

(72) Inventors: Derrick P. Fournier, Scarborough (CA); Henry A. Palma, Toronto (CA); Cameron Smyth, Toronto (CA)

(73) Assignee: 2351161 ONTARIO LIMITED, Scarborough, ON (CA)

( * ) Notice: Subject to any disclaimer, the term of this patent is extended or adjusted under 35 U.S.C. 154(b) by 182 days.

(21) Appl. No.: 14/419,094

(22) PCT Filed: Feb. 22, 2013

(86) PCT No.: PCT/CA2013/000159
§ 371 (c)(1),
(2) Date: Feb. 2, 2015

(87) PCT Pub. No.: WO2014/019061
PCT Pub. Date: Feb. 6, 2014

(65) Prior Publication Data
US 2015/0198548 A1    Jul. 16, 2015

(30) Foreign Application Priority Data
Aug. 3, 2012   (CA) .................................. 2784627

(51) Int. Cl.
| G01R 1/00 | (2006.01) |
| G01N 27/00 | (2006.01) |
| G01R 1/06 | (2006.01) |
| G01R 19/00 | (2006.01) |
| G01R 19/28 | (2006.01) |
| G01R 1/073 | (2006.01) |
| G01J 1/00 | (2006.01) |

(Continued)

(52) U.S. Cl.
CPC ............... *G01N 27/00* (2013.01); *G01R 1/06* (2013.01); *G01R 1/073* (2013.01); *G01R 19/00* (2013.01); *G01R 19/0084* (2013.01); *G01R 19/0092* (2013.01); *G01R 19/28* (2013.01); *B01J 20/00* (2013.01); *G01J 1/00* (2013.01); *G05B 1/00* (2013.01)

(58) Field of Classification Search
CPC ......... G01J 1/00; G05B 1/00; G05B 2219/00; B01J 2/00; B01J 20/00
See application file for complete search history.

(56) References Cited

U.S. PATENT DOCUMENTS 2,985,826 A * 5/1961 Fluegel ................ G01N 27/223
                                                  324/673
3,465,588 A * 9/1969 Slavin ..................... G01F 23/24
                                                  73/304 R

(Continued)

*Primary Examiner* — Jermele M Hollington
*Assistant Examiner* — Temilade Rhodes-Vivour (57) ABSTRACT

A measuring instrument for detection of electrical properties in a liquid includes a main body configured to hold a tester, a first pole extending from the main body, and a second pole extending from the main body that is spaced apart from the first pole. The first pole carries a positive probe for attachment to the tester, and the second pole carries a negative probe for attachment to the tester. When the probes are placed in the liquid, electrical properties in the liquid are detected by the tester.

19 Claims, 5 Drawing Sheets

(51) Int. Cl.
  *B01J 20/00*   (2006.01)
  *G05B 1/00*   (2006.01)

(56) References Cited

U.S. PATENT DOCUMENTS

| | | | | |
|---|---|---|---|---|
| 4,585,996 A * | 4/1986 | Luce | ............. | G01N 27/045 |
| | | | | 324/442 |
| 4,628,302 A * | 12/1986 | Barr | ............. | G01F 23/241 |
| | | | | 324/678 |
| 4,722,611 A * | 2/1988 | Hultgren | ............. | G01N 27/185 |
| | | | | 374/43 |
| 6,111,342 A * | 8/2000 | Muramatsu | ............. | G01N 29/036 |
| | | | | 310/311 |
| 2004/0058458 A1* | 3/2004 | Anker | ............. | G01N 33/58 |
| | | | | 436/526 |
| 2008/0264151 A1* | 10/2008 | Sullivan | ............. | G01N 13/04 |
| | | | | 73/64.47 |

* cited by examiner

MEASURING INSTRUMENT FOR DETECTION OF ELECTRICAL PROPERTIES IN A LIQUID

FIELD OF TECHNOLOGY

The present disclosure relates to electrical testers. Certain embodiments provide a measuring instrument for detection of electrical properties in a liquid.

BACKGROUND

Various techniques have been developed to deal with electrocution and electric shock hazards at boat docks and marinas. Hazards arise because power installations, either at shore or on boat locations, can leak electrical current into surrounding water. Causes of leakages include live power supply cords falling into the water, poorly insulated or corroded equipment, short circuit, mis-wiring, hot or active ground wires, stray voltage, or other electrical faults. It has been reported that two hundred cases of fatalities at marinas have occurred due to stray current leaking into surrounding water. Where leaked electrical current affects the muscles of a swimmer to cause or contribute to a drowning, the electric shock may not be revealed upon autopsy causing the threat to be hidden or under-reported. In addition to the threat to humans, pets, and aquatic marine life, the stray current can cause (metal) boats and marina objects to be corroded by electrolysis, and, in some circumstances, can spark fires.

A paper entitled "Worker Deaths by Electrocution" dated Can 1998 and published by the U.S. Department of Health and Human Services, Public Health Service, Centers for Disease Control and Prevention, National Institute for Occupational Health and Safety indicates that moisture increases the possibility of low-voltage electrocution. Swimming, standing in water, wearing wet clothing, high humidity, and perspiration all contribute to the risk. According to the NIOSH paper, under dry conditions, the resistance offered by the human body can be as high as 100,000 Ohms. Wet or broken skin can drop the body's resistance to 1,000 Ohms. An example illustrates how moisture affects low-voltage electrocutions: under dry conditions, Current=Volts/Ohms=120/100,000=1 mA, a barely perceptible level of current. Under wet conditions, Current=Volts/Ohms=120/1,000=120 mA, sufficient current to cause ventricular fibrillation. The NIOSH paper concludes that wet conditions are common during low-voltage electrocutions.

Attempts have been made to address some of the root causes of unwanted stray current being displaced into water, such as replacing equipment (household components such as power bars, extension cords, automotive battery chargers, etc.) with marine approved power cables and receptacles, or installing equipment such as circuit breakers, polarity indicators (to warn of reversed polarity), residual current devices such as ground fault circuit interrupters, electrical leakage circuit interrupters, isolation transformers, marine approved tinned stranded copper wires (not solid strand "house wire"), etc. However, equipment such as fuses or circuit breakers may not trip as the resistance of surrounding water may not allow the passage of sufficient current to blow a fuse or trip a circuit breaker.

Occurrences of stray current leakages into water persist and hazards are often difficult to detect and diagnose because few or no readily observable symptoms are present. There are even some reports of first responders attempting rescue but themselves succumbing to electrocution or electric shock, unaware that the first victim's swimming difficulties were caused or exacerbated by undetected stray current. In some situations, protective equipment such as insulating rubber boots or shoes (or other personal protective equipment or "PPE"), wooden planking that can be kept dry covering wet floors, etc. can be used, but this equipment is not convenient or suitable for use in many scenarios such as swimming in waters surrounding a marina.

Improvements in electrical testers and measuring instruments for detection of electrical properties in a liquid are desirable.

The foregoing examples of the related art and limitations related thereto are intended to be illustrative and not exclusive. Other limitations of the related art will become apparent to those of skill in the art upon a reading of the specification and a study of the drawings.

BRIEF DESCRIPTION OF THE DRAWINGS

Examples are illustrated with reference to the attached figures. It is intended that the examples and figures disclosed herein are to be considered illustrative rather than restrictive.

DETAILED DESCRIPTION

The following describes a measuring instrument for detection of electrical properties in a liquid that includes a main body configured to hold a tester, a first pole extending from the main body, and a second pole extending from the main body that is spaced apart from the first pole. The first pole carries a positive probe for attachment to the tester, and the second pole carries a negative probe for attachment to the tester. When the probes are placed in the liquid, electrical properties in the liquid are detected by the tester.

Throughout the following description, specific details are set forth in order to provide a more thorough understanding to persons skilled in the art. However, well-known elements may not be shown or described in detail to avoid unnecessarily obscuring the disclosure. Accordingly, the description and drawings are to be regarded in an illustrative, rather than a restrictive, sense.

This disclosure relates generally to electrical testers, and particularly to instruments and methods for detection of electrical properties in a liquid.

Marina fault simulations that include ground faults combined with dock ground system failures have substantiated the need for monitoring of the electrical condition of freshwater marinas. In situations of a ground faults, freshwater marinas pose a higher risk than saltwater marinas since salt water's high conductivity allows the majority of ground fault current to pass to the earth ground harmlessly. In freshwater or water with fewer impurities, the human body represents the low resistance path that the current is seeking to return to ground. The theoretical maximum electrical resistivity for water is about 182 kΩ·m at 25° C. A salt or acid contaminant level exceeding even 100 parts per trillion (ppt) in otherwise ultra-pure water begins to noticeably lower its resistivity by up to several kΩ·m.

When a human being is in the water, it takes very little electric current to cause muscle spasms or seizure. The NIOSH paper referenced above provides the estimated effects upon a human being of 60 Hz AC currents, reproduced at Table 1 of the present specification.

TABLE 1

Estimated Effects of 60 Hz AC Currents

| | |
|---|---|
| 1 mA | Barely perceptible |
| 16 mA | Maximum current an average man can grasp and "let go" |
| 20 mA | Paralysis of respiratory muscles |
| 100 mA | Ventricular fibrillation threshold |
| 2 Amps | Cardiac standstill and internal organ damage |
| 15/20 | Amps Common fuse or breaker opens circuit* |

*Contact with 20 milliamps of current can be fatal. As a frame of reference, a common household circuit breaker can be rated at 15, 20, or 30 amps.

Currents on the order of 50 milliamps (0.05 amps) sustained for 2 seconds, or 500 milliamps sustained for just 0.2 seconds, can, in certain circumstances, cause ventricular fibrillation. Currents as low as 5 milliamps can cause muscle seizure. Dangerous voltage levels need not be high when current is flowing through water. The electrical resistance of the human body is 1000 to =100

Nigel Calder's Boatowner's Mechanical and Electrical Manual, $2^{nd}$ Ed., 1996, McGraw-Hill provides an example of a fault current situation. If a boat that is connected to shore-side power using an extension cord has the grounding pins cut off and a piece of equipment using AC current develops a short, the fault current, denied a path to ground through the normal ground wire, can run to ground through a bonded underwater fitting. The fault current can develop a field around the boat. At the fitting that is discharging the current into the water the voltage can be at the full fault voltage (e.g. as high as 240 volts). Resistance within the water can cause the voltage to decrease the further the distance from the boat until ground potential (i.e., 0 volts) is reached. Depending on the water's resistance and other factors, there can be a voltage gradient, creating a declining voltage the farther the distance from the boat. A swimmer entering this electrical field will have one part of his or her body at one voltage potential, and other parts at another potential. According to Calder, if the voltage differential that is bridged is great enough, the electric current will pass through the body. And, if the voltage gradient is above 2 volts per foot (6 volts per meter), the situation can be potentially lethal.

Quite small leakage currents and voltages can be deadly, particularly in freshwater environments. An analysis of freshwater marinas by J. D. Shafer and D. Rifkin entitled Freshwater Marinas: A Ground Fault Analysis, 2002, indicates that water resistance in a large, well-maintained marina facility located on a freshwater reservoir in the southeastern United States was about 50 ohms. In a simulation of a single 30 amp, 120 volt shore cable and an induced 5.2 amp ground fault between a boat's hot and ground legs and a ground on the boat is disabled, by which current flow into water was measured by clamping the cable with an ammeter, the voltage at various distances from the electrified boat were measured. The depth of the water was about 18 feet. Directly behind the boat, 42-52 volts were measured about 1 foot from the outdrive (portion of the boat engine that is outside the hull, providing steering and propulsion), 11 volts were measured 10 feet from the boat, 3 volts were measured 20 feet from the boat, 1.3 volts were measured 30 feet from the boat, 72 volts were measured directly astern, across the dock, about 10 feet away, and 4.5 volts were measured on a dock adjusting cable 15 feet from the boat (measured between the cable and a copper probe in the water near the cable). The analysis indicated that the electric field was strong enough directly behind the boat (2-3-2.8 volts per foot) to be potentially lethal to a swimmer entering the waters in this field, and other areas further from the boat, would be felt as a shock or tingle that could cause injuries or death.

While media reports and research efforts have established that potentially lethal electric fields can be established near and around affected boats and dock structures, instruments for measuring or detecting various electrical properties in marina waters, including sources of energy, offering convenience and/or portability (and improvements therein) remain and/or are desirable.

Figure 1:
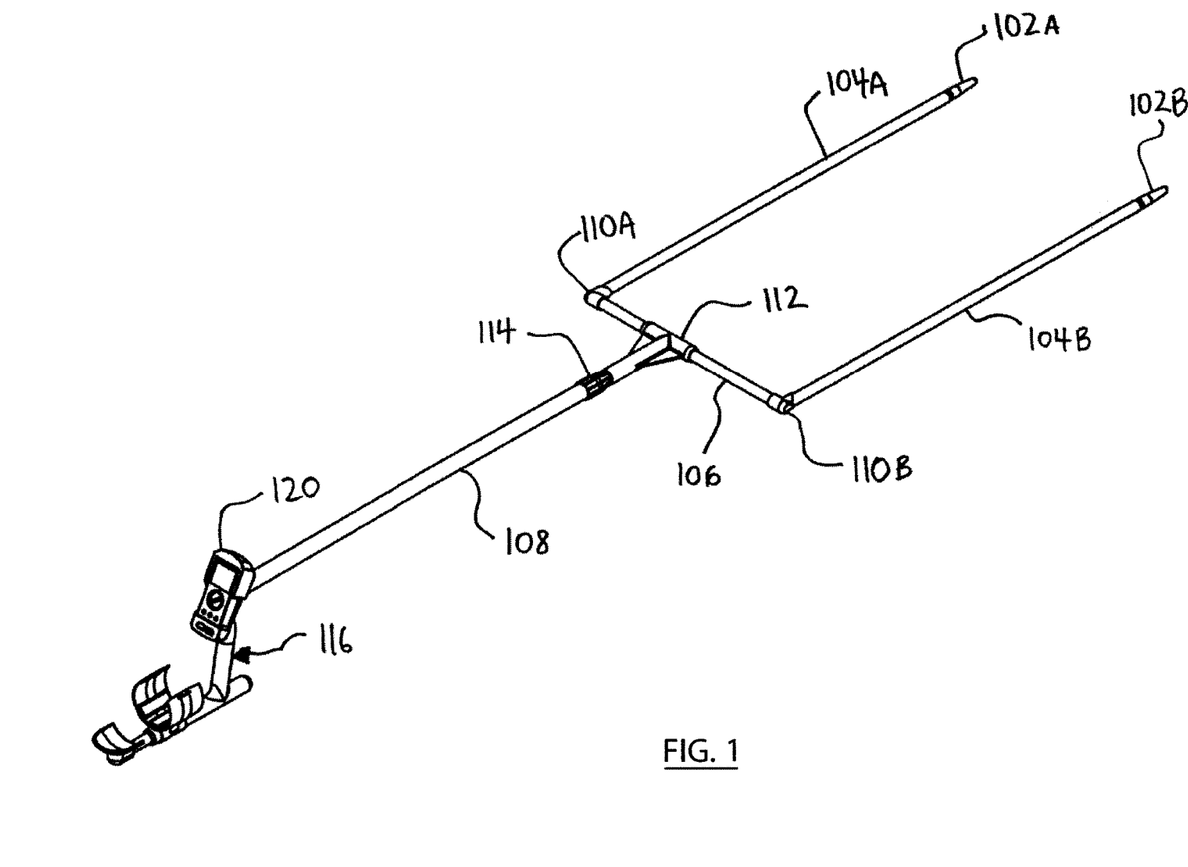
FIG. 1 is a perspective view of a measuring instrument in accordance with an example.

A perspective view of an example of a measuring instrument 100 for detection of electrical properties, more specifically safe electrical properties, in a liquid is shown in FIG. 1. The measuring instrument 100 includes a main body 108. In the example of FIG. 1, portions of the main body 108 can be tubular (i.e., include a shaft) and can include an interior passage (i.e., using "hollow construction"). The main body 108 can be "telescoping" and include an inner shaft (or shafts) that slides out from an outer shaft (or shafts). A cuff 114 secures the inner and outer shafts. The cuff 114 can be tapered and have inner threading that matches threads on the inner and/or outer shafts. In one example, the main body 108 is made of insulating or non-conductive material such as ABS plastic. A vibrant colour can be selected for high visibility.

According to one example, an extended length of the main body 108 is between about 24 inches to about 240 inches (and all sub-ranges therebetween), or more specifically, about 60 inches to about 180 inches, or even more specifically, about 120 inches (10 feet). The distance permits marina waters, etc. to be accessed from a distance. Where the main body 108 is telescoping, the length of the measuring instrument can be adjusted for better fit to access the water, and for portability.

The main body 108 includes a tester holder 120 that is configured to hold a tester 124. In one example, the tester 124 can be detachable from the tester holder 120. The tester holder 120 is adjustable and fits a wide range of testers. According to other examples, the tester 124 can be integrated with the main body 108 or another component of the measuring instrument 100.

According to one example, the tester 124 can be an electrical meter or a multimeter, and more specifically, a digital multimeter. A multimeter is an instrument that combines several measurement functions in one device. A typical multimeter measures electric current, voltage, and usually resistance, typically over several ranges of value. The multimeter can include a display to indicate the quantity measured. The multimeter can include an embedded computer and provide enhanced functions including auto-ranging, auto-polarity, graphical representations of quantities under test on the display, etc. Use of the term "tester" in the present specification is intended to encompass any device or apparatus that is capable of measuring electrical properties such as current and voltage. The tester 124 has multiple leads for voltage measurement and for current measurement. "Current" refers to the flow of electrons from a source of voltage through a conductor and is measured in amperes (Amps). "Voltage" is the fundamental force or pressure that causes electricity to flow through a conductor and is measured in volts. "Gradient voltage" refers to the voltage per unit of length along a resistor or other conductive path. In the example of FIG. 1, the tester 124 has three leads: Common, V/mA, and A.

Still with reference to FIG. 1, the measuring instrument 100 includes a spreader bar 106 that extends from the main body 108 in a substantially transverse or perpendicular direction. A fitting 112, which can be T-shaped, joins the spreader bar 106 to the main body 108. The fitting 112 can permit rotation of the spreader bar 106 (and poles 104) by about 360 degrees (about 180 degrees in either direction). Other rotation values or ranges are encompassed within the scope of the present specification. The fitting 112 can include a flange or stop (not shown) to prevent over-rotation. In one example, the spreader bar 106 is tubular (i.e., a shaft), includes an interior passage, and is made from non-conductive material such as ABS plastic. As well, the fitting 112 can include interior passage(s), and be made from non-conductive material such as ABS plastic. Use of a spreader bar 106 and a fitting 112 is exemplary; it will be appreciated that, in other examples according to the present specification, the poles 104 (discussed below) can be connected to the main body 108 directly or in any other suitable configuration.

The measuring instrument 100 further includes two poles 104A and 104B (or arms) that extend from the spreader bar 106 (individually referred to as "pole 104" and collectively as "poles 104"). In one example, a width of the spreader bar 106 is between about 6 inches to about 36 inches (and all sub-ranges therebetween), or more specifically, about 24 inches. The width of the spreader bar 106 can determine the spacing apart of the poles 104. Preferably, the poles 104 are spaced apart about 24 inches permitting the measuring instrument 100 to be fitted inside manhole covers to access a sewer, for example. As well, a measurement of about 2 volts or higher per 12 inches can be considered lethal (as discussed above); accordingly, this form factor permits a convenient display of gradient voltage that is potentially lethal.

In the example of FIG. 1, each pole 104 is connected to the spreader bar 106 by an elbow connector 110 (e.g. also being tubular and having an interior passage) (individually referred to as "elbow connector 110" and collectively as "elbow connectors 110"). In other examples according to the present specification, different configurations of connectors or fasteners can be used.

Each pole 104A and 104B carries one of two probes 102A and 102B (individually referred to as "probe 102" and collectively as "probes 102") for selective attachment to the tester 124. Typically, one of the probes 102A and 102B is a negative probe and the other of the probes 102A and 102B is a positive probe. According to one example, the probes 102 include a conductive material, more specifically metal, such as insulated wires or coaxial cables. In one example, the negative probe (e.g. probe 102A) can be coloured black, and the positive probe (e.g. probe 102B) can be coloured red. Alternatively, a portion of the elbow connector 110A or pole 104A associated with the negative probe 102A can be coloured black, while a portion of the elbow connector 110B or pole 104B associated with the positive probe 102B can be coloured red. Other indicators for the positive and negative probes can be used, to facilitate ready identification of the negative and positive probes, in accordance with the present specification.

Each probe 102 has two ends. The first end is connected (or capable of connection) to one or more leads of the tester 124, for example, being wired through the interior passage of the poles 104 (and other components of the main body 108) and the second end is connected to a probe end (discussed below). The hollow construction of the measuring instrument 100 (or components thereof) permits internal wiring of the probes 102 to the tester 124. The interior passages can permit twisting of the probes to facilitate rotation (discussed above) or folding (discussed below).

In one example, the poles 104 can be tubular (i.e. shafts) and each include an interior passage. The probes 102 can travel along the length of the poles 104 and/or the main body 108 on the outside or within one or more of the interior passages of the poles 104 and the main body 108 (including the spreader bar 106).

Figure 5:
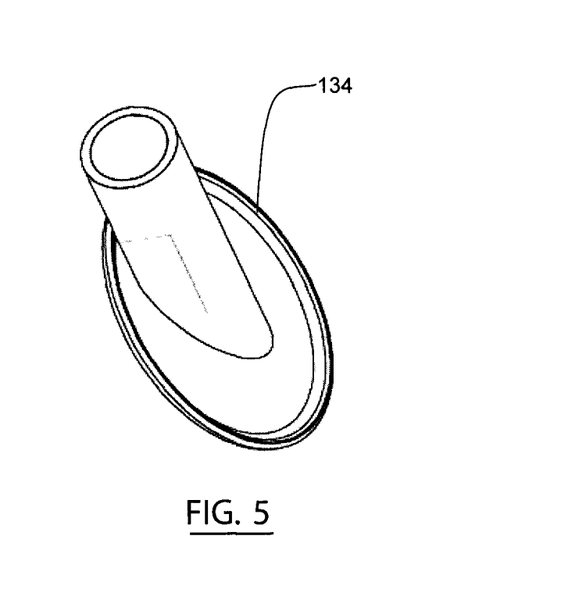
FIG. 5 is a perspective view of a probe disk for use with the measuring instrument of FIG. 1.

According to one example, the probe ends can be flat disks 134 (shown in FIG. 5) or flat tips made of a conductive material, more specifically, metal, and more specifically, aluminum. Other probe ends can be employed such as bare wires, alligator clips, and the like. The probe ends can be interchangeable.

Still with reference to FIG. 1, the measuring instrument 100 includes a grip assembly 116 connected to the main body 108 permitting handheld operation of the measuring instrument 100. In one example, the grip assembly features three point contact for maneuverability (hand grip, forearm grip, and elbow contact).

Figure 2:
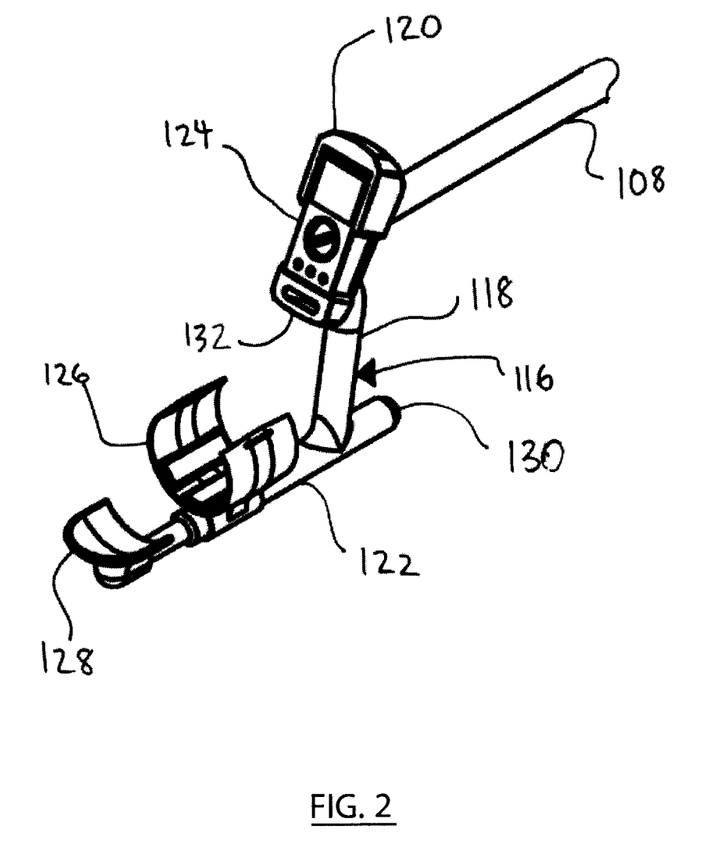
FIG. 2 is an enlarged perspective view of the measuring instrument of FIG. 1.

FIG. 2 is an enlarged perspective view of the measuring instrument 100, including details for the grip assembly 116. As shown in FIG. 2, the grip assembly 116 includes a hand grip bar 118, an elbow bar 122, a forearm grip 126, an elbow contact 128, and a mount 130. The main body 108 can be connected (e.g., by a hand grip bar 118) to an elbow bar 122 that is disposed to be parallel to the main body 108. The hand grip bar 118 is gripped by an operator during measurement operations. The elbow bar 122, which can include a forearm grip 126, extends in parallel to the operator's forearm during measurement operations. The forearm grip 126 and an adjustable elbow contact 128 accommodate and support the operator's forearm and elbow to allow for steady measurement operations and for greater ease of use. The forearm grip 126 can include a strap (not shown) to prevent slippage of the measuring instrument 100 during use. The forearm grip 126 and/or the elbow contact 128 can include one or more cushions (e.g. made of silicone rubber) for added precision during measurement and/or ease of use. The mount 130 can be used to mount a secondary device such as a flashlight or storage. In one example, a flashlight can be integrated in the measuring instrument 100. The measuring instrument 100 can thus be used with one arm leaving the operator with a free hand for adjusting the tester 124, length of the measuring instrument 100, angles of the probe ends, and the grip assembly 116.

Figure 3A:
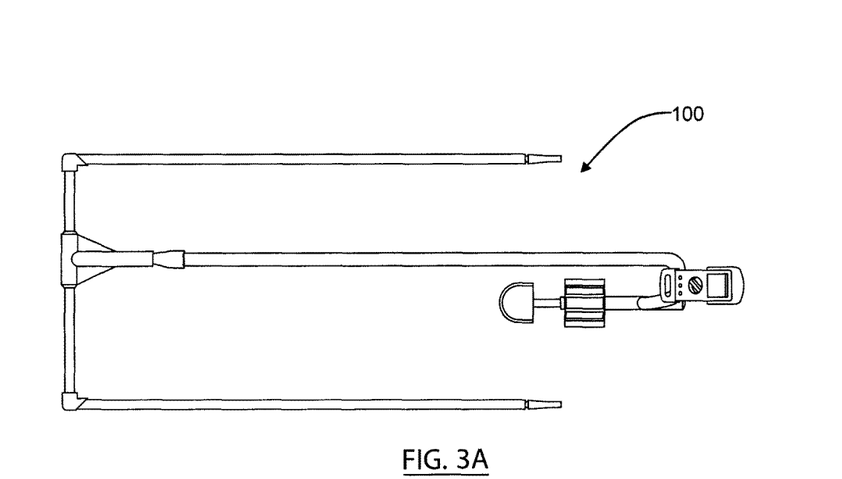
FIG. 3A is a top plan view of the measuring instrument of FIG. 1 in a folded position.
Figure 3B:
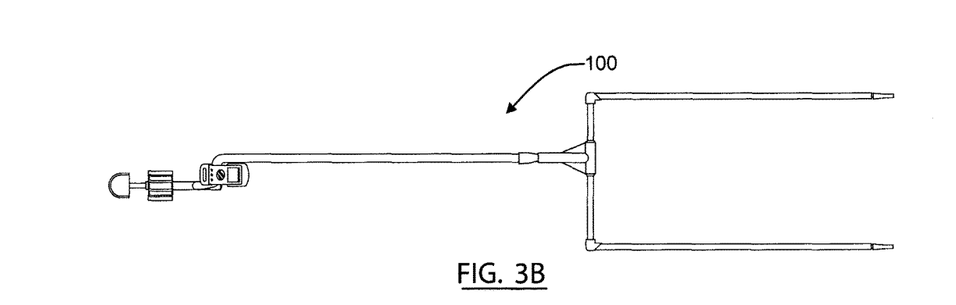
FIG. 3B is a top plan view of the measuring instrument of FIG. 1 in an unfolded position.
Figure 3C:
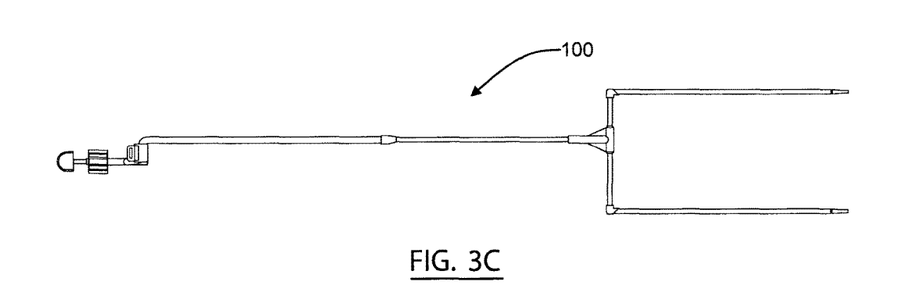
FIG. 3C is a top plan view of the measuring instrument of FIG. 1 in an unfolded and extended position.

As shown in FIG. 3A through FIG. 3C, each of the poles 104 and grip assembly 116 can be folded toward the main body 108. FIG. 3A is a top plan view of the measuring instrument 100 in a folded position. In FIG. 3B, the poles 104 and the grip assembly 116 are unfolded. In FIG. 3C, the main body 108 is extended. Accordingly, the poles 104 can be folded for compact transportation. Moreover, the angle of the poles 104 relative to the main body 108 can be adjusted for improved function and performance.

In operation, the probe ends are placed in a liquid or aqueous solution, such as waters surrounding a marina, and one or more electrical properties in the liquid are detected by the tester 124. When probes (i.e., electrodes) are placed in an electrolyte (i.e., the water) and a voltage is present, the electrolyte will conduct electricity that can be measured. The measuring instrument 100 can be used in any location with water and wherein the electrical potential does not exceed a maximum voltage and current rating of the tester 124, including flooded rooms, flooded basements, storage vaults, sewers, illuminated pools, whirlpool baths, hot tubs, or fountains, and the like. According to one example, the measuring instrument 100 can be used around boats and docks to locate electricity leaking into the surrounding water.

Typically, the measuring instrument 100 is used to search and locate gradient voltage and stray current passing through the water. Using the grip assembly 116, the probe ends are submerged into the water and the tester 124 can be turned and is ready for use. The tester 124 should read zero volts and zero amperage. When the probes 102 are placed in liquid, the detected electrical properties are one of voltage across the probes, and current through the probes.

If gradient voltage or electrical current is present in the liquid, then the electricity will choose the path of least resistance and travel in the first probe, through the wire to a lead of the tester 124, pass through the tester 124 down an opposite lead of the tester, and out the second probe. Accordingly, the tester 124 will indicate the presence and amount of electrical current detected in the water. Electricity to the surrounding boats, docks, equipment, etc. can be switched off until the source of the electricity getting into the water is located.

Upon "sweeping" the measuring instrument 100 across the waters under test with the probes 104 submerged, including having one of the probes 104 in contact with a portion of the boat or marina objects, the tester 124 can indicate fluctuations in the quantities under test. According to one example, where the quantities under test include gradient voltage, the quantities can increase during sweeping as the measuring instrument 100 gets closer to an electrical source. After sweeping and detecting a "local maximum" for the quantities under test, rotation of the measuring instrument 100 by 90 degrees can be expected to achieve a "zero" reading indicating the source of energy to a right angle of the plane extending from the poles. In other words, by rotating the measuring instrument 100 (using the grip assembly 116) in a 360 degree circle, the quantities displayed by the tester 124 can increase and decrease to reveal the direction of the electrical current path, aiding in locating the source of electricity (as travelling towards or away from the measuring instrument 100), with positive and negative indicators on the tester 124. Upon rotation of the measuring instrument in the liquid, the detected voltage or the detected current increases in proximity of the probes 102 to an electrical source. A measuring instrument according to the present specification can thus, at least in part, aid in the detection of unsafe stray current, thereby improving safety and reducing the risk of electrocution, electric shocks, burns, etc. to swimmers, pets, aquatic marine life in marinas, first responders, etc.

Figure 4:
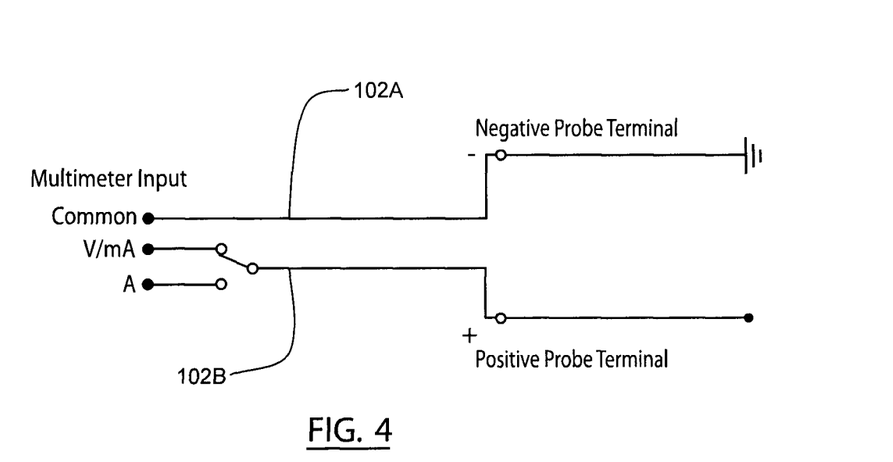
FIG. 4 is a schematic view of probes for selective attachment to a tester of the measuring instrument of FIG. 1.

According to one example, the tester holder 120 includes a tester switch 132 that changes attachment of the probes 102 to the leads of the tester 124 from voltage measurement to current measurement. A schematic view of the probes 102 for selective attachment to the tester 124 is shown in FIG. 4. The safety of the operator is thus at least partially ensured because direct contact with the probes can be avoided. For example, as shown in FIG. 4, the negative probe 102A can be connected to the "Common" lead of the tester 124, while the tester switch 132 can selectively connect the positive probe 102B to the "V/mA" lead of the tester 124 for measurement of voltage, or to the "A" lead of the tester 124 for measurement of current (amperage). Activation of the tester switch 132 changes the attachment from voltage measurement to current measurement, and vice versa.

The measuring instrument 100 is used to detect gradient voltage and electrical current passing through water around boats and docks as a result of electricity leaking into the water. Electricity leaks occur due to short circuit, improper wiring, hot or active ground wires, and other faults such as improperly rigged or insulated power cords. Use of the measuring instrument can aid in the detection of safe electrical properties and contribute to the reduction of electrocution to swimmers and aquatic marine life in marinas, and in the reduction of corrosion to boats and marina objects caused by electrolysis. Over 200 cases per year are reported of persons drowning in and around marinas. Evidence is reportedly mounting that at least some fatalities classified as drownings were, in fact, caused by electric shocks. The measuring instrument 100 can be used by first responders in such locations as lighted pools or fountains, flooded basements and other areas (including after hurricanes or other natural disasters), onshore power installations having underground vaults, fire fighters performing fireground operations near downed power lines (solid-stream water applications), etc. The hazard appears to be greater in fresh water that is electrified by a boat or other machinery leaking electricity.

Figure 6:
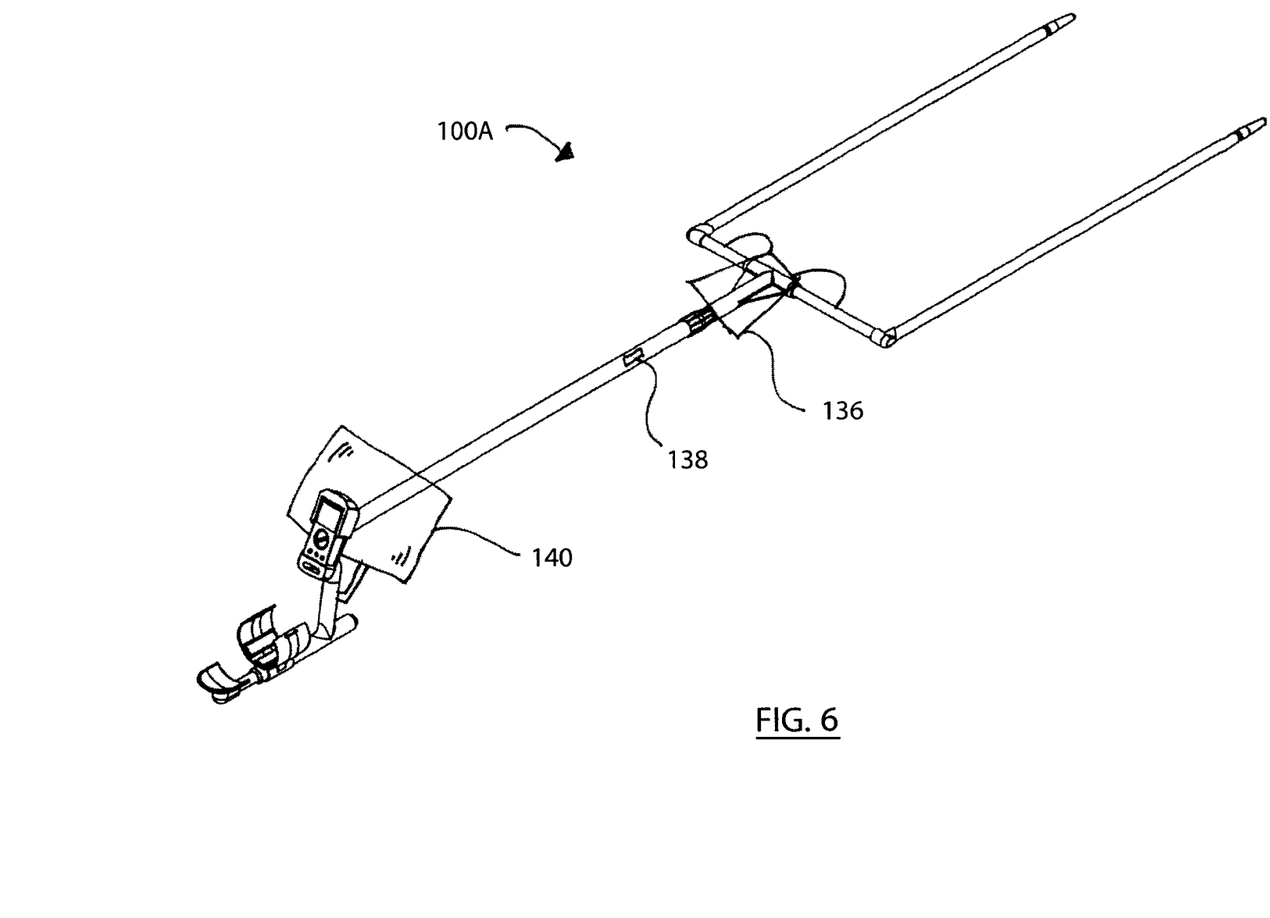
FIG. 6 is a perspective view of a measuring instrument in accordance with a further example, for high voltage applications.

According to another example shown in FIG. 6 of a measuring instrument 100A for use in high voltage applications (e.g. in the utility industry), the main body 108 can be made of a fiberglass material. The grip assembly 116 can include a plexiglass visor 140. A 25:1 reduction coil 136 and an internal fuse 138 can be positioned between the probes 102 and the tester 124 to permit the tester 124 to test voltages in the range 13,800 volts. These modifications, which are exemplary and not intended to be limiting, enables the measuring instrument 100A to be used in high voltage scenarios by utility industry technicians and the like.

A measuring instrument for detection of electrical properties, more specifically safe electrical properties, in a liquid includes a main body configured to hold a tester, a first pole extending from the main body, and a second pole extending from the main body that is spaced apart from the first pole. The first pole carries a positive probe for attachment to the tester, and the second pole carries a negative probe for attachment to the tester. When the probes are placed in the liquid, electrical properties in the liquid are detected by the tester.

The tester has a plurality of leads and the probes can be selectively attached to the leads for one of voltage measurement, and current measurement. When the probes are placed in the liquid, the detected electrical properties are one of: voltage across the probes, and current through the probes.

Upon movement of the measuring instrument in the liquid, as by rotation of the poles, the detected voltage or the detected current increases in proximity of the probes to an electrical source. During rotation, the probes are uniformly spaced apart, advantageously enabling a direction of the electrical source to be detected by the tester.

The main body of the measuring instrument includes a telescoping shaft and a transverse spreader bar connected to the telescoping shaft. The probes extend from the spreader bar and the first and second poles are spaced apart by the spreader bar. The spreader bar has a width in the range of about six (6) inches to about thirty six (36) inches, and more specifically, about twenty four (24) inches. An extended length of the telescoping shaft is in the range of about twenty four (24) inches to about two hundred forty (240) inches, and more specifically, about one hundred sixty eight (168) inches.

The main body, the telescoping shaft, and the spreader bar include a non-conductive material, more specifically an ABS plastic material, and the probes include a conductive material, more specifically, a metal material.

One or more of the main body, the telescoping shaft, the spreader bar, and the poles include tubes having an interior passage, and the probes are at least partially disposed in the interior passage of the tubes. The poles can be rotated or folded about the spreader bar, and the interior passage of the tubes permit twisting of the probes to facilitate said rotation or folding.

The measuring instrument further includes a grip assembly connected to the main body permitting handheld operation of the measuring instrument.

The probes include detachable probe ends. The probe ends can be metal tips or flat disks.

The tester can be a multimeter. The tester can be integrated with the main body.

The measuring instrument can be used in any location with water and wherein the electrical potential does not exceed a maximum voltage and current rating of the tester. The measuring instrument can be used in a marina, a flooded room, a flooded basement, a storage vault, a sewer, a pool, a hot tub, a whirlpool bathtub, and a fountain, among other locations.

A measuring instrument for detection of electrical properties in water includes a main body having an interior passage, the main body configured to hold a multimeter, wherein the multimeter has a plurality of leads and the probes can be selectively attached to the leads for one of voltage measurement, and current measurement, a telescoping shaft of non-conductive material having an interior passage, a transverse spreader bar of non-conductive material having an interior passage and connected to the telescoping shaft, a grip assembly connected to the main body permitting handheld operation of the measuring instrument, a first pole of non-conductive material having an interior passage extending from the spreader bar, and a second pole of non-conductive material having an interior passage extending from the spreader bar that is spaced apart from the first pole, the first pole carrying a positive probe of conductive material for attachment to the multimeter, and the second pole carrying a negative probe of conductive material for attachment to the multimeter, wherein the probes are disposed in one or more of said interior passages, and wherein when the probes are placed in the water, voltage across the probes, and current through the probes in the water are detected by the multimeter.

While a number of exemplary aspects and examples have been discussed above, those of skill in the art will recognize certain modifications, permutations, additions and sub-combinations thereof.

What is claimed is:

1. A measuring instrument for detection of electrical properties in a liquid comprising:
    a main body configured to hold a tester;
    a first pole extending from the main body; and
    a second pole extending from the main body that is spaced apart from the first pole,
    the first pole carrying a positive probe for attachment to the tester, and the second pole carrying a negative probe for attachment to the tester,
    wherein when the probes are placed in the liquid and the poles are rotated, electrical properties in the liquid, acting as a variable potential resistor, are detected by the tester.

2. The measuring instrument of claim 1 wherein the tester has a plurality of leads and the probes can be selectively attached to the leads for one of voltage measurement, and current measurement, and when the probes are placed in the liquid, the detected electrical properties are one of: voltage across the probes, and current through the probes.

3. The measuring instrument of claim 2 wherein upon rotation of the poles in the liquid, the detected voltage or the detected current increases in proximity of the probes to an electrical source.

4. The measuring instrument of claim 1 wherein during rotation of the poles, the probes are uniformly spaced apart enabling a direction of the electrical source to be detected by the tester.

5. The measuring instrument of claim 1, wherein the tester is a multimeter.

6. The measuring instrument of claim 1, wherein the tester is integrated with the main body.

7. The measuring instrument of claim 1 wherein the liquid is water and the measuring instrument is for use in any location with water and wherein the electrical potential does not exceed a maximum voltage and current rating of the tester.

8. The measuring instrument of claim 7 for use in one of: a marina, a flooded room, a flooded basement, a storage vault, a sewer, a pool, a hot tub, a whirlpool bathtub, and a fountain.

9. A measuring instrument for detection of electrical properties in a liquid comprising:
    a main body configured to hold a tester;
    a first pole extending from the main body; and
    a second pole extending from the main body that is spaced apart from the first pole, the first pole carrying a positive probe for attachment to the tester, and the second pole carrying a negative probe for attachment to the tester,
    wherein the main body comprises a telescoping shaft and a transverse spreader bar connected to the telescoping shaft, wherein the probes extend from the spreader bar and the first and second poles are spaced apart by the spreader bar; and
    wherein when the probes are placed in the liquid, electrical properties in the liquid are detected by the tester.

10. The measuring instrument of claim 9, wherein a width of the spreader bar is in the range of about 6 inches to about 36 inches, and an extended length of the telescoping shaft is in the range of about 24 inches to about 240 inches.

11. The measuring instrument of claim 10, wherein the width of the spreader bar is about 24 inches, and the extended length of the telescoping shaft is about 168 inches.

12. The measuring instrument of claim 9, wherein the main body, the telescoping shaft, and the spreader bar comprise a non-conductive material, and the probes comprise a conductive material.

13. The measuring instrument of claim 12, wherein the non-conductive material comprises an ABS plastic material, and the conductive material comprises a metal material.

14. The measuring instrument of claim 13, wherein one or more of the main body, the telescoping shaft, the spreader bar, and the poles comprise tubes having an interior passage, and the probes are at least partially disposed in the interior passage of the tubes.

15. The measuring instrument of claim 14, wherein the poles can be rotated or folded about the spreader bar, and the interior passage of the tubes permit twisting of the probes to facilitate said rotation or folding.

16. The measuring instrument of claim 15, wherein the measuring instrument further comprises a grip assembly connected to the main body permitting handheld operation of the measuring instrument.

17. The measuring instrument of claim 16, wherein the probes comprise detachable probe ends.

18. The measuring instrument of claim 17, wherein the probe ends comprise one of: metal tips and flat disks.

19. A measuring instrument for detection of electrical properties in water comprising:
- a main body having an interior passage, the main body configured to hold a multimeter, wherein the multimeter has a plurality of leads and the probes can be selectively attached to the leads for one of voltage measurement, and current measurement;
- a telescoping shaft of non-conductive material having an interior passage;
- a transverse spreader bar of non-conductive material having an interior passage and connected to the telescoping shaft;
- a grip assembly connected to the main body permitting handheld operation of the measuring instrument;
- a first pole of non-conductive material having an interior passage extending from the spreader bar; and
- a second pole of non-conductive material having an interior passage extending from the spreader bar that is spaced apart from the first pole;
- the first pole carrying a positive probe of conductive material for attachment to the multimeter, and the second pole carrying a negative probe of conductive material for attachment to the multimeter, wherein the probes are disposed in one or more of said interior passages, and wherein when the probes are placed in the water, voltage across the probes, and current through the probes in the water are detected by the multimeter.

* * * * *